US010219810B2

(12) United States Patent
Mimran (10) Patent No.: US 10,219,810 B2
(45) Date of Patent: Mar. 5, 2019

(54) SURGICAL INSTRUMENT SYSTEM AND METHOD

(71) Applicant: Warsaw Orthopedic, Inc, Warsaw, IN (US)

(72) Inventor: Ronnie Isaac Mimran, San Ramon, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 280 days.

(21) Appl. No.: 15/019,710

(22) Filed: Feb. 9, 2016

(65) Prior Publication Data
US 2016/0235418 A1 Aug. 18, 2016

Related U.S. Application Data

(60) Provisional application No. 62/116,771, filed on Feb. 16, 2015.

(51) Int. Cl.
*A61B 17/16* (2006.01)
*A61F 2/46* (2006.01)

(52) U.S. Cl.
CPC ...... *A61B 17/1633* (2013.01); *A61B 17/1631* (2013.01); *A61B 17/1659* (2013.01); *A61B 17/1671* (2013.01); *A61F 2/4603* (2013.01); *A61F 2/4607* (2013.01)

(58) Field of Classification Search
CPC .. A61F 2/4603; A61F 2/4607; A61B 17/1631; A61B 17/1659; A61B 17/1633
See application file for complete search history.

(56) References Cited

U.S. PATENT DOCUMENTS

| 2,429,356 | A | * | 10/1947 | Hicks | A61B 17/1633 433/116 |
| 3,384,085 | A | * | 5/1968 | Hall | A61B 17/1633 606/180 |
| 3,835,858 | A | * | 9/1974 | Hagen | A61B 17/1633 408/141 |
| 4,813,413 | A | * | 3/1989 | Gray | A61B 17/00 606/84 |
| 5,443,471 | A | * | 8/1995 | Swajger | A61B 17/1659 403/294 |
| 5,468,245 | A | * | 11/1995 | Vargas, III | A61B 17/8808 606/192 |
| 6,063,088 | A | * | 5/2000 | Winslow | A61B 17/025 606/279 |
| 6,113,605 | A | * | 9/2000 | Storer | A61F 2/4607 606/86 R |
| 6,277,121 | B1 | * | 8/2001 | Burkinshaw | A61B 17/1677 606/80 |
| 8,162,967 | B1 | * | 4/2012 | Kaiser | A61B 17/1604 279/82 |
| 9,192,393 | B2 | * | 11/2015 | Piferi | A61B 17/16 |
| 9,414,848 | B2 | * | 8/2016 | Edwards | A61B 17/16 |
| 9,610,083 | B2 | * | 4/2017 | Kuntz | A61B 17/1642 |
| 9,629,730 | B2 | * | 4/2017 | Reiley | A61F 2/4202 |
| 9,770,306 | B2 | * | 9/2017 | Hagag | A61B 34/30 |
| 9,826,985 | B2 | * | 11/2017 | Slobitker | A61B 17/1631 |

(Continued)

*Primary Examiner* — Christian Sevilla (57) ABSTRACT

A surgical instrument includes an actuator. A member is connected with the actuator and includes a mating part releasably engageable with a tissue engaging element such that the member is interchangeable with a plurality of alternate tissue engaging elements. Systems, implants and methods are described.

13 Claims, 4 Drawing Sheets

(56) References Cited

U.S. PATENT DOCUMENTS

| | | | | |
|---|---|---|---|---|
| 2003/0055404 A1* | 3/2003 | Moutafis | A61B 17/1633 | 604/540 |
| 2003/0097133 A1* | 5/2003 | Green | A61B 17/1617 | 606/80 |
| 2003/0220646 A1* | 11/2003 | Thelen | A61B 17/164 | 606/79 |
| 2004/0010262 A1* | 1/2004 | Parkinson | A61F 2/4607 | 606/99 |
| 2005/0177168 A1* | 8/2005 | Brunnett | A61B 17/1624 | 606/80 |
| 2005/0203527 A1* | 9/2005 | Carrison | A61B 17/1604 | 606/80 |
| 2005/0273167 A1* | 12/2005 | Triplett | A61B 17/1671 | 623/17.11 |
| 2006/0111723 A1* | 5/2006 | Chapolini | A61B 17/1622 | 606/80 |
| 2007/0233131 A1* | 10/2007 | Song | A61B 17/1671 | 606/79 |
| 2008/0255574 A1* | 10/2008 | Dye | A61F 2/4603 | 606/99 |
| 2010/0286694 A1* | 11/2010 | Rio | A61B 17/162 | 606/80 |
| 2011/0129292 A1* | 6/2011 | Chen | F16J 15/061 | 403/72 |
| 2011/0245833 A1* | 10/2011 | Anderson | B23B 49/02 | 606/80 |
| 2012/0029545 A1* | 2/2012 | Nelson | A61B 17/1624 | 606/171 |
| 2012/0089146 A1* | 4/2012 | Ferko | A61B 17/1617 | 606/87 |
| 2012/0109229 A1* | 5/2012 | Forsell | A61B 17/1615 | 606/86 R |
| 2012/0191094 A1* | 7/2012 | Alain | A61B 17/1642 | 606/80 |
| 2013/0211408 A1* | 8/2013 | Kather | A61B 17/1617 | 606/83 |
| 2016/0235418 A1* | 8/2016 | Mimran | A61B 17/1671 | |

* cited by examiner

SURGICAL INSTRUMENT SYSTEM AND METHOD

CROSS-REFERENCE TO RELATED APPLICATION

This application claims the benefits of U.S. Provisional Patent Application No. 62/116,771, filed Feb. 16, 2015, the contents of which being hereby incorporated in its entirety by reference.

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. For example, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior technologies.

SUMMARY

In one embodiment, a surgical instrument is provided. The surgical instrument includes an actuator. A member is connected with the actuator and includes a mating part releasably engageable with a tissue engaging element such that the member is interchangeable with a plurality of alternate tissue engaging elements. In some embodiments, systems, implants and methods are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system are discussed in terms of medical devices for the treatment of musculoskeletal disorders and more particularly, in terms of a surgical system for treating a spine at a surgical site and a method for treating a spine. In some embodiments, the systems and methods of the present disclosure are employed with a spinal joint and fusion, for example, with a cervical, thoracic, lumbar and/or sacral region of a spine.

In some embodiments, the present system includes a surgical instrument configured to remove spinal disc tissue, such as, for example, nucleus pulposus and/or cartilaginous end plates for a spinal fusion procedure. In some embodiments, the present system includes an automated surgical instrument configured to prepare an intervertebral disc space in connection with a surgical procedure. In some embodiments, the surgical instrument is employed with a method for treating a spine to remove tissue to facilitate creation of a cavity in the tissue at a surgical site to place mechanical and/or biologic materials in the cavity for a fusion across an intervertebral disc space. In some embodiments, the surgical instrument includes a hand-held instrument. In some embodiments, the present system and methods avoid the repetitive nature of disc space preparation that can lead to fatigue and inadequate removal of tissue and preparation of the intervertebral disc space. In some embodiments, the present system and methods avoid the hazards associated with surgery adjacent sensitive anatomy, such as, for example, nerve roots and/or the spinal cord.

In some embodiments, the surgical instrument is electrically powered. In some embodiments, the surgical instrument is electrically powered to decrease surgeon variability and allows for complete removal and effective preparation of the intervertebral disc space. In some embodiments, the surgical instrument is employed with a method to treat a spine that decreases the time to prepare the intervertebral disc space with less movement adjacent sensitive anatomy, as described herein. In some embodiments, the surgical instrument is employed with a method to treat a spine that decreases surgeon fatigue.

In some embodiments, the present system and methods include a powered surgical instrument that utilizes one or more working ends to remove tissue, such as, for example, nucleus tissue and endplate tissue. In some embodiments, the present system comprises a kit or set that includes one or more working ends. In some embodiments, the present system comprises working ends, which may include, for example, a soft, wire-brush working end for engagement with nucleus tissue and a rigid, drum-rasp working end for engagement with endplate tissue. In some embodiments, the present system comprises working ends, which may include, for example, one or more of a soft, wire-brush, a rigid, drum-rasp, a rotating paddle, a shaver and/or a reamer. In some embodiments, the present system comprises a working end that is configured for tissue removal and harvest for use in the surgical procedure, or biopsy for pathological analysis.

In some embodiments, the present system includes an electrical power source connected with a cord to a hand-piece of the surgical instrument. In some embodiments, the electrical power source comprises a standard wall socket and has a port for plugging the cord from the hand-piece to transfer electrical energy to the hand-piece. In some embodiments, the surgical instrument may include electronics for variable speed rotation/operation. In some embodiments, the surgical instrument includes a hand-piece with a trigger, which is electrically connected with the surgical instrument to receive electrical energy from the power source via the cord and converts it to mechanical energy. In some embodiments, the trigger controls speed of rotation/operation. For example, when a surgeon depresses the trigger, the energy conversion results in the working ends rotating, according to the settings provided on the power source.

In some embodiments, the surgical instrument includes a quick connect dock for the working ends. In some embodiments, the dock attaches to the hand-piece and comprises a dock/receptacle for attaching different and/or alternate working ends. In some embodiments, the surgical instrument includes a wire brush working end. In some embodiments, a cylindrical wire brush working end is engaged with the quick connect dock. In some embodiments, the surgical instrument includes a drum rasp working end. In some embodiments, the drum rasp working end has a rigid cylinder with cutting/shaving blades on its surface that is placed into the quick connect dock. In some embodiments, the surgical instrument includes a rotating shaver working end. In some embodiments, the surgical instrument includes a paddle shaped working end with cutting blades on its edges that is placed into the quick connect dock. In some embodiments, the surgical instrument includes a rotating shaver working end. In some embodiments, the surgical instrument includes a reamer working end. In some embodiments, the surgical instrument includes a hollow drill working end that is placed into the quick connect dock. In some embodiments, the surgical instrument includes a safety sleeve. In some embodiments, the safety sleeve includes a thin rigid protective tube that is attached to the quick connect dock and slides over each of the working ends.

In some embodiments, the present system is employed with a method for treating a spine including the step of connecting a power source with a standard wall outlet for electrical power. In some embodiments, the method includes the step of attaching a cord from the power source to the hand-piece. In some embodiments, the method includes the step of attaching the quick connect dock and the safety sleeve to the hand-piece. In some embodiments, the method includes the step of selecting and docking one of the working ends into the quick connect dock. In some embodiments, the method includes the step of activating the power and adjusting the settings on the power source. In some embodiments, the method includes the step of manipulating the hand-piece. In some embodiments, the method includes the step of sliding the safety sleeve over the working end. In some embodiments, the method includes the step of inserting the working end into the desired cavity and retracting the sleeve. In some embodiments, the method includes the step of activating the trigger, which rotates the exposed working end within a tissue cavity.

In some embodiments, the present system includes a surgical instrument that is assembled by selecting a working end from a plurality or kit of working ends and placing the selected working end into the quick connect dock with the safety sleeve attached. In some embodiments, the working end connected with the dock and the safety sleeve are connected with the hand-piece as an assembly. In some embodiments, the hand-piece is designed to convert the electrical energy from the power source and the cord into mechanical energy to drive the rotational movement in a controlled fashion. In some embodiments, the working ends are selected based on tissue, cavity configuration, anatomy and/or surgical site location.

In some embodiments, the surgical instrument includes a dual working end, which is double-sided, allowing for two different working ends on one surgical instrument. In some embodiments, the quick connect dock is configured for connection with a dual working end. In some embodiments, the working end is flexible. In some embodiments, the working end includes a spheroidal or universal joint. In some embodiments, the working end includes an angled shape to allow for working around corners and other anatomical hindrances. In some embodiments, the surgical instrument includes robotic control and/or surgical navigation of the working ends.

In some embodiments, the present system is employed with a method for treating a spine that includes the step of assembling the surgical instrument and manipulating the surgical instrument. In some embodiments, the method includes the step of placing the sleeve in the tissue cavity. In some embodiments, the surgeon retracts the sleeve and depresses the trigger on the hand-piece such that the working end begins to rotate. In some embodiments, the tissue is removed and/or tissue surfaces are prepared.

In some embodiments, one or all of the components of the present system may be disposable, peel pack and/or pre packed sterile devices. One or all of the components of the system may be reusable. The system may be configured as a kit with multiple sized and configured components.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 1:
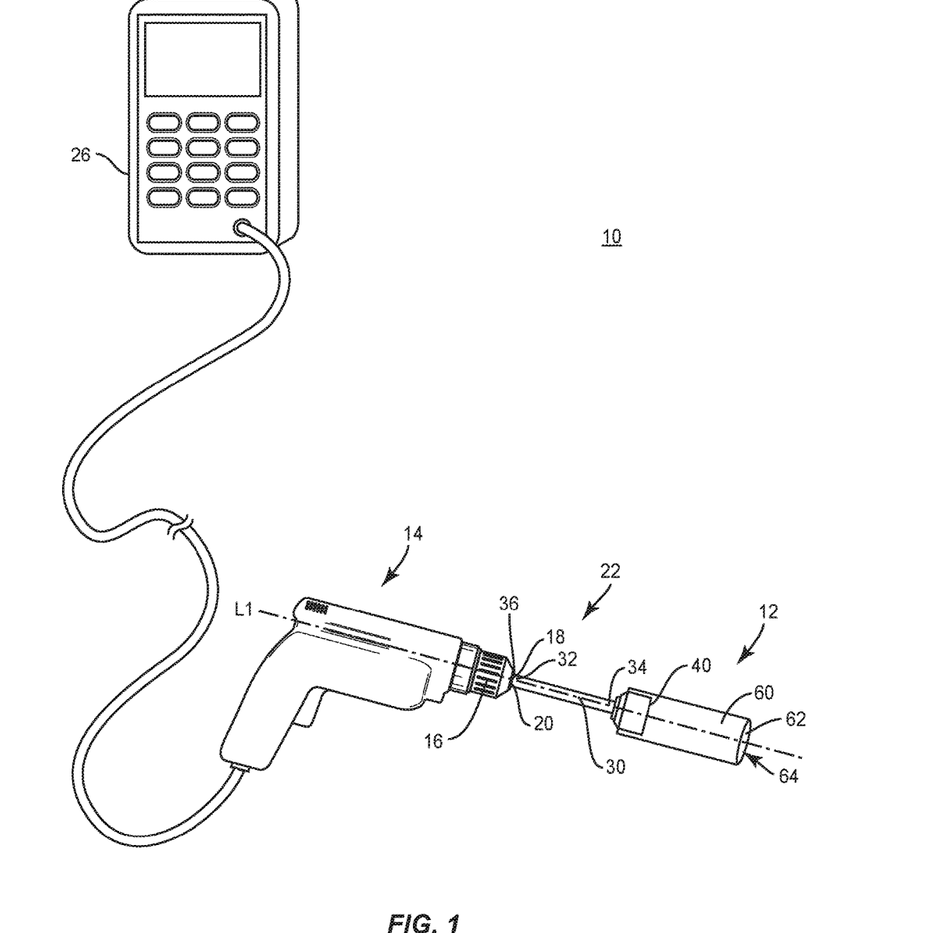
FIG. 1 is a perspective view of components of one embodiment of a surgical system in accordance with the principles of the present disclosure.
Figure 2:
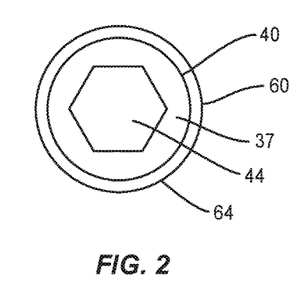
FIG. 2 is an end view of components of the system shown in FIG. 1.
Figure 3:
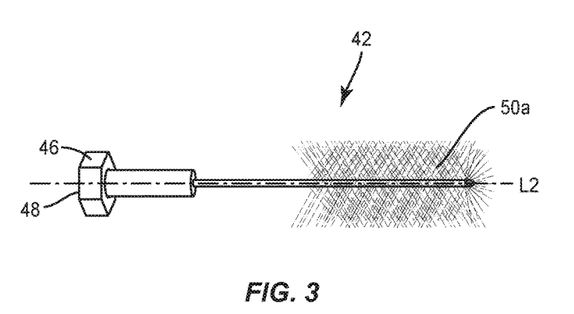
FIG. 3 is a side view of components of one embodiment of a surgical system in accordance with the principles of the present disclosure.

The following discussion includes a description of a surgical system including surgical instruments, related components and methods of employing the surgical system. Alternate embodiments are also disclosed. Reference is made in detail to the exemplary embodiments of the present disclosure, which are illustrated in the accompanying figures. Turning to FIGS. 1-3, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Figure 11:
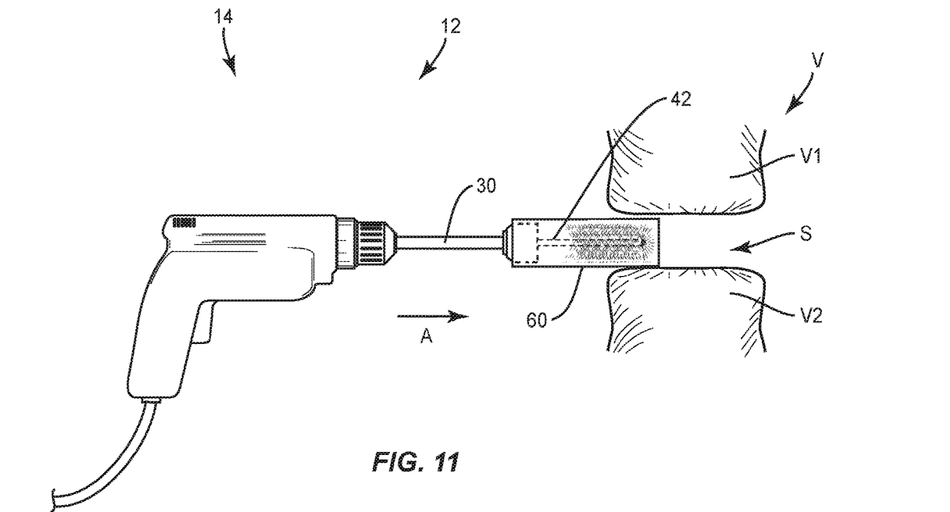
FIG. 11 is a perspective view of components of one embodiment of a surgical system in accordance with the principles of the present disclosure disposed with vertebrae.
Figure 12:
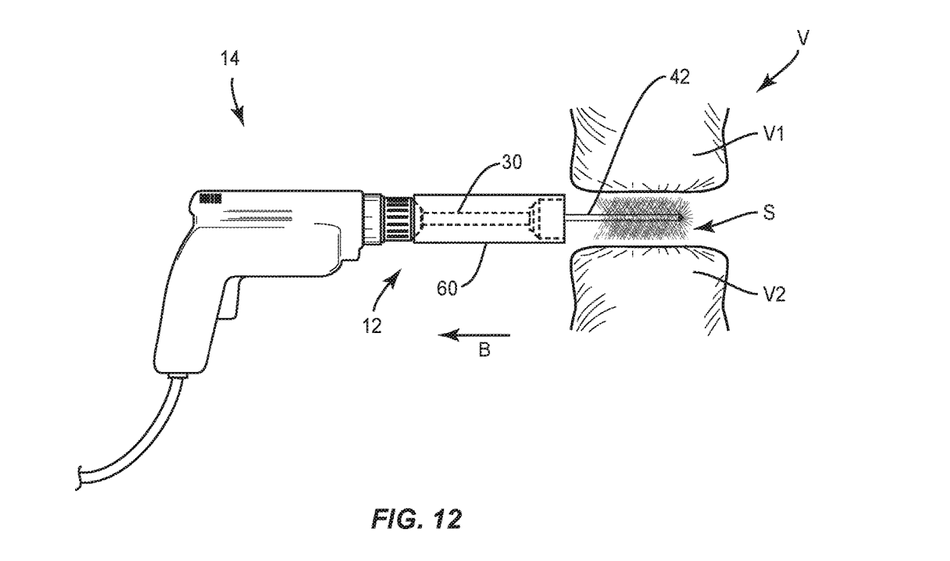
FIG. 12 is a perspective view of components of one embodiment of a surgical system in accordance with the principles of the present disclosure disposed with vertebrae.

Surgical system 10 is employed, for example, with a fully open surgical procedure, a minimally invasive procedure including percutaneous techniques, and mini-open surgical techniques to deliver and introduce instrumentation and/or a spinal implant at a surgical site of a patient, which includes, for example, a spine having vertebrae V, as shown in FIGS. 11 and 12. In some embodiments, the spinal implant can include one or more components of one or more spinal constructs, such as, for example, cages, spacers, vertebral devices, bone fasteners, spinal rods, connectors and/or plates.

Surgical system 10 includes a surgical instrument 12. Surgical instrument 12 includes an actuator, such as, for example, a motorized actuator 14. Actuator 14 includes a mating part, such as, for example, a chuck 16. Chuck 16 includes an inner surface, such as, for example a socket 18. Socket 18 defines a cavity 20 and is configured to mate with a member, such as, for example, a member 22, as described herein. In some embodiments, socket 18 defines a cavity cross-section, such as, for example, oval, oblong, triangular, square, polygonal, irregular, uniform, non-uniform, arcuate, variable and/or tapered. In some embodiments, socket 18 may have alternate surface configurations to enhance fixation with member 22 such as, for example, rough, arcuate, undulating, mesh, porous, semi-porous, dimpled and/or textured. In some embodiments, socket 18 and/or member 22 comprise a quick release configuration such that socket 18 and member 22 are releasably fixable without tools, via a biasing member, manipulable, detents, clamps and/or keyed.

In some embodiments, actuator 14 includes an electric drill motor disposed within a housing of actuator 14 for rotating socket 18 and member 22. In some embodiments, actuator 14 is connected with a cord to a power source 26. In some embodiments, actuator 14 may be pneumatic, hydraulic and/or include a handle for hand rotation. In some embodiments, actuator 14 may include, such as, for example, a powered drill, a hand drill or other tool. In some embodiments, actuator 14 is connected with power source 26, which is connected to an electrical outlet (not shown). In some embodiments, power source 26 includes a battery. In some embodiments, the battery is powered from an external device via telemetry (near-field communication, for example). In some embodiments, power source 26 includes a pneumatic power source, such as, for example, a compressed air device. In some embodiments, power source 26 includes a compressed air cartridge. In some embodiments, power source 26 includes a hydraulic power source.

Member 22 includes a shaft 30. Shaft 30 extends between an end 32 and an end 34, and defines a longitudinal axis L1. End 32 includes a portion, such as, for example, a fitting 36 configured to mate with and engage socket 18 of chuck 16. Fitting 36 comprises a shape complimentary to cavity 20 to provide a releasably fixed engagement between actuator 14 and shaft 30. In some embodiments, fitting 36 may include a hexagonal, triangular, polygonal, star or hexalobe cross sectional configuration to engage a correspondingly shaped portion of socket 18. Actuator 14 rotates shaft 30 and retains fitting 36 therewith via an engagement member, such as, for example, a friction fit, detent, locking keyway and/or biasing members. Actuator 14 is configured to rotate surgical instrument 12, as described herein. Shaft 30 is selectively disengageable from socket 18 via the particular engagement members employed. In some embodiments, shaft 30 is configured to mate with alternate actuators.

In some embodiments, fitting 36 is connected with socket 18 via a keyed joint connection. In some embodiments, fitting 36 includes a resilient flange (not shown) configured to mate with a corresponding shaped portion in socket 18, such as, for example, a keyseat. In some embodiments, other keyway configurations are contemplated, such as, for example, oval, oblong, triangular, square, hexagonal, polygonal, irregular, uniform, non-uniform and/or tapered. In some embodiments, the keyed joint resists and/or prevents relative rotation between shaft 30 and actuator 14 and enables torque transmission.

End 34 includes a surface 37 that defines a mating part 40. Mating part 40 is configured for releasable engagement with a tissue engaging element, such as, for example, a surgical working end 42, as described herein. In some embodiments, mating part 40 is configured to engage working end 42 in a quick release configuration, as described herein. In some embodiments, mating part 40 and/or working end 42 comprises a quick release configuration such that mating part 40 and end 42 are releasably fixable without tools, via a biasing member, manipulable, detents, clamps and/or keyed, to facilitate intra-operative interchangeability of member 22 with one, a plurality, a kit and/or a set of ends 42, as described herein. In some embodiments, mating part 40 is interchangeable with a plurality of alternate ends 42 during a surgical procedure, as described, to perform different or alternate steps for treating tissue.

In some embodiments, mating part 40 includes a female mating portion 44. In some embodiments, working end 42 includes a surface 46 that defines a corresponding male mating portion 48, as described herein. In some embodiments, the quick release configuration facilitates intra-operative disengagement of working end 42 from member 22 during a surgical procedure.

In some embodiments, female mating portion 44 may include a spheroidal joint connection with male mating portion 48. In some embodiments, female mating portion 44 may include a hexagonal, triangular, polygonal, star or hexalobe cross sectional configuration for engaging a correspondingly shaped portion of male mating portion 48. In some embodiments, female mating portion 44 may include a chuck, collet or other mating structure. In some embodiments, male mating portion 48 has diameter that creates a friction fit with surface 37 of female mating portion 44. In some embodiments, all or only a portion of surface 37 and/or surface 46 may have alternate surface configurations to enhance engagement with one another such as, for example, rough, arcuate, undulating, mesh, porous, semi-porous, dimpled and/or textured. Female mating portion 44 is configured to mate with alternate working ends 42 as required for a particular surgical procedure, as described herein. In some embodiments, mating part 40 is configured to provide a dock and/or a receptacle for attaching various working ends 42 in a quick release configuration, as described herein.

In some embodiments, male mating portion 48 of working end 42 defines an axis L2. Mating part 40 is configured to guide and/or align male mating portion 48 into female mating portion 44 into the quick release configuration. In some embodiments, connection of working end 42 with mating part 40 aligns axis L2 along axis L1. In some embodiments, working end 42 is configured for an articulated connection with mating part 40. In some embodiments, connection of working end 42 with mating part 40 disposes axis L2 in alternate orientations relative to axis L1, such as, for example, transverse, perpendicular and/or other angular orientations such as acute or obtuse. In some embodiments, working end 42 is configured for an articulated connection with mating part 40.

Figure 4:
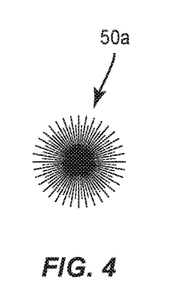
FIG. 4 is an end view of the components shown in FIG. 3.
Figure 5:
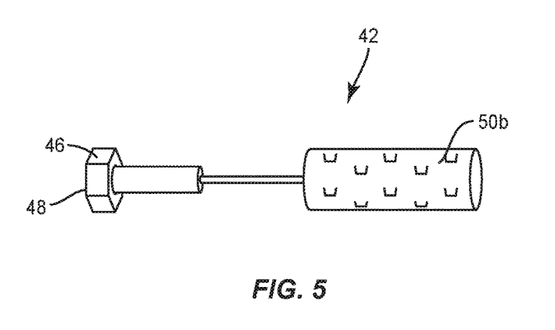
FIG. 5 is a side view of components of one embodiment of a surgical system in accordance with the principles of the present disclosure.
Figure 6:
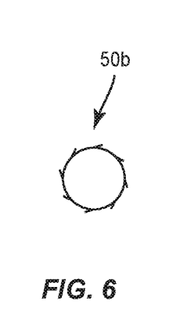
FIG. 6 is an end view of the components shown in FIG. 5.
Figure 7:
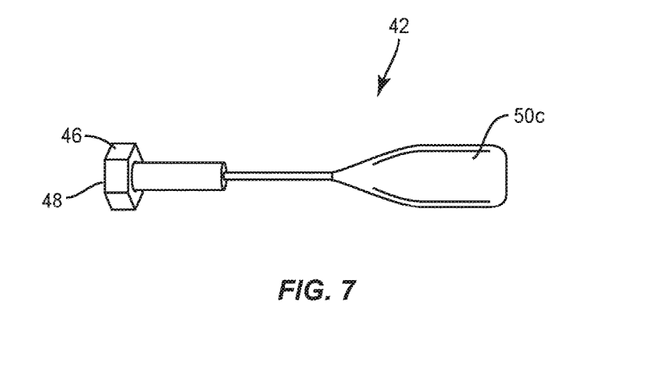
FIG. 7 is a side view of components of one embodiment of a surgical system in accordance with the principles of the present disclosure.
Figure 8:
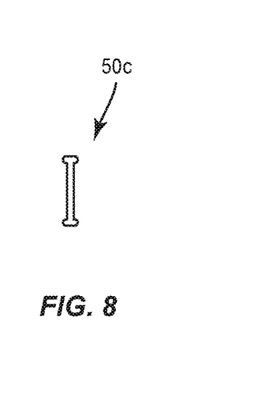
FIG. 8 is an end view of the components shown in FIG. 7.
Figures 9, 10:
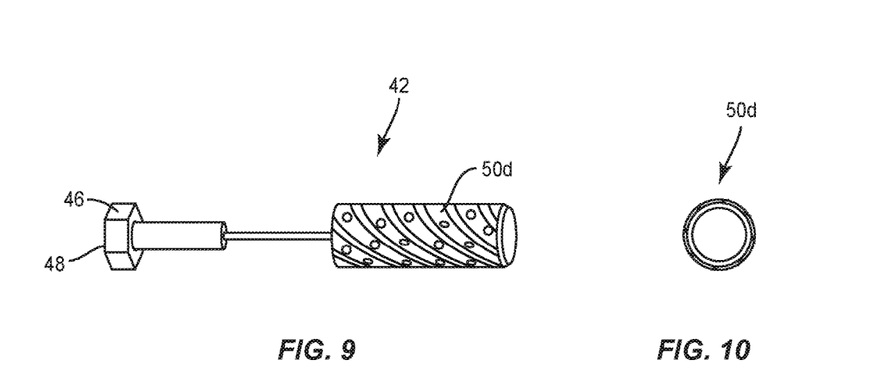
FIG. 9 is a side view of components of one embodiment of a surgical system in accordance with the principles of the present disclosure.
FIG. 10 is an end view of the components shown in FIG. 9.

In some embodiments, a working end 42 includes, for example, a wire brush 50a, as shown in FIGS. 3 and 4. In some embodiments, wire brush 50a includes a cylindrical wire brush configured to engage tissue, as described herein. In some embodiments, a working end 42 includes, for example, a drum rasp 50b, as shown in FIGS. 5 and 6. In some embodiments, drum rasp 50b includes a rigid cylinder having cutting and/or shaving blades configured to engage tissue, as described herein. In some embodiments, a working end 42 includes, for example, a rotating cutter 50c, as shown in FIGS. 7 and 8. In some embodiments, rotating cutter 50c includes a paddle shaped portion having cutting blades disposed along the paddle edges configured to engage tissue, as described herein. In some embodiments, a working end 42 includes, for example, a reamer 50d, as shown in FIGS. 9 and 10. In some embodiments, reamer 50d includes a hollow drill that is configured to engage tissue, as described herein.

Working end 42 is configured for an interchangeable engagement with mating part 40 to facilitate utilization of the various working ends. In some embodiments, working end 42 is configured for selection from a plurality of tissue engaging elements such that working end 42 is connectable with a compatible member 22. In some embodiments, working end 42 includes a first working end and a second working end forming a dual working end configuration. In some embodiments, the dual working end configuration includes two working ends extending from one side of member 22. In some embodiments, the dual working end configuration includes a working end extending from one side of member 22 and a working end extending from an opposing side of member 22. In some embodiments, one or a plurality of working ends extend from one side of member 22.

In some embodiments, surgical instrument 12 includes a sleeve 60 that is connected with member 22. Sleeve 60 includes a surface 62 that defines a cavity 64. Cavity 64 is configured for disposal of working end 42 when sleeve 60 is oriented in an extended position, as described herein. Sleeve 60 is configured for axial translation along axis L2 relative to member 22. Sleeve 60 is translatable in an axial direction to an extended position, as shown by arrow A in FIG. 11, and in an axial direction to a retracted position, as shown by arrow B in FIG. 12. In some embodiments, in the extended position, working end 42 is encased within sleeve 60 to resist and/or prevent contact of a working end with tissue during insertion of surgical instrument 12 to a surgical site. In some embodiments, in the retracted position, sleeve 60 is oriented to expose working end 42 to tissue such that working end 42 engages, manipulates and or removes tissue at a surgical site, as described herein.

In some embodiments, member 22 includes an image guide, such as, for example, a navigation component (not shown) configured to generate a signal representative of a position of one or more components of surgical instrument 12, for example, working end 42. The navigation component is configured for disposal with one or more components of surgical instrument 12, for example, a portion of member 22. In some embodiments, the navigation component may be integrally formed with member 22 and/or working end 42. In some embodiments, the navigation component is attachable with member 22 prior to the surgical procedure.

In some embodiments, the navigation component may include one or a plurality of guides. In some embodiments, the navigation component is shaped substantially like a letter X and comprises four spaced apart arms including emitters for generating a signal representing the trajectory of working end 42 relative to a portion of a patient's anatomy and the depth of working end 42 within the patient's anatomy. In some embodiments, the navigation component includes at least one light emitting diode. In some embodiments, the navigation component may include other tracking devices capable of being tracked by a corresponding sensor array, such as, for example, a tracking device that actively generates acoustic signals, magnetic signals, electromagnetic signals, radiologic signals.

In some embodiments, surgical system 10 includes a tracking device having an emitter array that generates signals representing the position of various body reference points of the patient's anatomy. A sensor (not shown) receives signals from the navigation component and the emitter array. The sensor communicates with a processor, such as, for example, a digitizer control unit (not shown), which processes the signals from the navigation component and the emitter array to provide information regarding the trajectory of working end 42 relative to a portion of the patient's anatomy and the depth of working end 42 within the patient's anatomy. The processor sends this information to a monitor (not shown), which provides a visual representation of the position of working end 42 relative to the patient's anatomy to allow the medical practitioner to guide working end 42 to a desired location within the patient's anatomy.

The monitor is configured to generate an image from a data set stored in a controller, such as, for example, a computer. In some embodiments, the data set may be generated preoperatively using scanning techniques, such as, for example, a CAT scanner or MRI scanner. The image data set includes reference points for at least one body part, such as, for example, the spine of a patient, which have a fixed spatial relation to the body part. The processor is connected to the monitor, under control of the computer, and to working end 42.

The sensor receives and triangulates signals generated by the navigation component and the emitter array to identify the relative position of each of the reference points and working end 42. The processor and the computer modify the image data set according to the identified relative position of each of the reference points during the procedure. The position and trajectory of working end 42 provided by the navigation component and the emitter array is processed by the processor and the computer and is visually displayed against the preoperative image data set stored in the computer to provide the medical practitioner with a visual representation of the trajectory of working end 42 relative to a portion of the patient's anatomy and the depth of working end 42 within the patient's anatomy.

In assembly, operation and use, surgical system 10, similar to the systems and methods described herein, including surgical instrument 12 is employed with a surgical procedure for treatment of a spinal disorder affecting a section of a spine of a patient, as discussed herein. For example, surgical instrument 12 can be used with a surgical procedure for treatment of a condition or injury of an affected section of the spine including vertebrae V, as shown in FIGS. 11 and 12. In some embodiments, one or more components of surgical system 10 can be delivered or implanted as a pre-assembled device or can be assembled in situ. Surgical system 10 may be completely or partially revised, removed or replaced.

The components of surgical system 10 can be employed with a surgical treatment, for example, a fusion across an intervertebral space S of vertebrae V and/or an interbody fusion of an applicable condition or injury of an affected section of a spinal column and adjacent areas within a body. In some embodiments, surgical system 10 may be employed with other surgical procedures, such as, for example, discectomy, laminotomy, laminectomy, nerve root retraction, foramenotomy, facetectomy, decompression, and spinal, nucleus or disc replacement.

In some embodiments, the components of surgical system 10 may be employed with one or a plurality of vertebra, such as, for example, vertebra V1 and vertebra V2. To treat a selected section of vertebrae V, a medical practitioner obtains access to a surgical site including vertebrae V in any appropriate manner, such as through incision and retraction of tissues. In some embodiments, the components of surgical system 10 can be used in any existing surgical method or technique including open surgery, mini-open surgery, minimally invasive surgery and percutaneous surgical implantation, whereby vertebrae V are accessed through a mini-incision, or sleeve that provides a protected passageway to the area. Once access to the surgical site is obtained, the particular surgical procedure can be performed for treating the spine disorder. In some embodiments, surgical system 10 can be used to provide support and stabilize vertebrae V.

In some embodiments, the components of surgical system 10 are employed to remove some or all of the disc tissue adjacent intervertebral space S including the disc nucleus and fluids, adjacent tissues and/or bone, which may include corticating, scraping and/or removing tissue from the surfaces of endplates of opposing vertebrae V1, V2, as well as for aspiration and irrigation of the region.

An incision is made in the body of a patient and a cutting instrument (not shown) creates a surgical pathway for delivery of components of surgical system 10 including surgical instrument 12 adjacent intervertebral space S. In some embodiments, the components of surgical system 10 include a surgical kit, which comprises a plurality of working ends 42 that are interchangeable and compatible with member 22. Member 22 is intra-operatively interchangeable with the plurality of alternate working ends 42 during the surgical procedure to perform different or alternate steps for treating vertebrae V.

Actuator 14 is engaged with shaft 30 such that fitting 36 mates with socket 18. Sleeve 60 is disposed in an initial, retracted position to facilitate assembly with a selected working end 42 with member 22 in a quick release configuration. Working end 42 is selected for intra-operative interchangeable employment of one of the plurality of working ends 42 provided for engaging the tissue adjacent intervertebral space S including nucleus pulposus and/or cartilaginous end plates.

In some embodiments, a working end 42 includes a wire brush 50*a*, as shown in FIGS. 3 and 4, and is selected for engagement with nucleus tissue adjacent intervertebral space S. Male mating portion 48 of working end 42 having wire brush 50*a* is releasably connected with female mating portion 44 of member 22 in a quick release configuration. Sleeve 60 is translated, in a direction shown by arrow A in FIG. 11, into the extended position to enclose wire brush 50*a* to resist and/or prevent engagement of wire brush 50*a* with tissue. Wire brush 50*a* is disposed adjacent intervertebral space S. Sleeve 60 is translated, in a direction shown by arrow B in FIG. 12, into the retracted position to expose wire brush 50*a*. Surgical instrument 12 is manipulated such that wire brush 50*a* engages and/or disrupts the nucleus tissue. In some embodiments, the disrupted tissue is removed. Sleeve 60 is translated, in a direction shown by arrow A in FIG. 11, into the extended position to enclose wire brush 50*a* to resist and/or prevent engagement of wire brush 50*a* with tissue. In some embodiments, surgical instrument 12 is manipulated to remove wire brush 50*a* from adjacent intervertebral space S and/or the surgical site. Sleeve 60 is translated, in a direction shown by arrow B in FIG. 12, into the retracted position to expose wire brush 50*a*. The quick release interchangeability of mating part 40 and end 42 facilitate disengagement of wire brush 50*a* from member 22, as described herein, such that an alternate working end may be intra-operatively interchanged and engaged with member 22 to perform an alternate step for treating vertebrae V. In some embodiments, a ronguer may also be employed to engage nucleus tissue.

In some embodiments, a working end 42 includes a drum rasp 50*b*, as shown in FIGS. 5 and 6, and is selected for engagement with endplate tissue adjacent intervertebral space S. Male mating portion 48 of working end 42 having drum rasp 50*b* is releasably connected with female mating portion 44 of member 22 in a quick release configuration. Sleeve 60 is translated, in a direction shown by arrow A in FIG. 11 into the extended position to enclose drum rasp 50*b* to resist and/or prevent engagement of drum rasp 50*b* with tissue. Drum rasp 50*b* is disposed adjacent intervertebral space S. Sleeve 60 is translated, in a direction shown by arrow B in FIG. 12, into the retracted position to expose drum rasp 50*b*. Surgical instrument 12 is manipulated such that drum rasp 50*b* engages and/or disrupts the endplate tissue. In some embodiments, the disrupted tissue is removed. Sleeve 60 is translated, in a direction shown by arrow A in FIG. 11, into the extended position to enclose drum rasp 50*b* to resist and/or prevent engagement of drum rasp 50*b* with tissue. In some embodiments, surgical instrument 12 is manipulated to remove drum rasp 50*b* from adjacent intervertebral space S and/or the surgical site. Sleeve 60 is translated, in a direction shown by arrow B in FIG. 12, into the retracted position to expose drum rasp 50*b*. The quick release interchangeability of mating part 40 and end 42 facilitate disengagement of drum rasp 50*b* from member 22, as described herein, such that an alternate working end may be intra-operatively interchanged and engaged with member 22 to perform an alternate step for treating vertebrae V.

In some embodiments, a working end 42 includes a rotating cutter 50*c*, as shown in FIGS. 7 and 8, and is selected for engagement with tissue adjacent intervertebral space S. Male mating portion 48 of working end 42 having rotating cutter 50*c* is releasably connected with female mating portion 44 of member 22 in a quick release configuration. Sleeve 60 is translated, in a direction shown by arrow A in FIG. 11, into the extended position to enclose rotating cutter 50*c* to resist and/or prevent engagement of rotating cutter 50*c* with tissue. Rotating cutter 50*c* is disposed adjacent intervertebral space S. Sleeve 60 is translated, in a direction shown by arrow B in FIG. 12, into the retracted position to expose rotating cutter 50*c*. Surgical instrument 12 is manipulated such that rotating cutter 50*c* engages and/or disrupts the endplate tissue. In some embodiments, the disrupted tissue is removed. Sleeve 60 is translated, in a direction shown by arrow A in FIG. 11, into the extended position to enclose rotating cutter 50*c* to resist and/or prevent engagement of rotating cutter 50*c* with tissue. In some embodiments, surgical instrument 12 is manipulated to remove rotating cutter 50*c* from adjacent intervertebral space S and/or the surgical site. Sleeve 60 is translated, in a direction shown by arrow B in FIG. 12, into the retracted position to expose rotating cutter 50*c*. The quick release interchangeability of mating part 40 and end 42 facilitate disengagement rotating cutter 50*c* from member 22, as described herein, such that an alternate working end may be intra-operatively interchanged and engaged with member 22 to perform an alternate step for treating vertebrae V.

In some embodiments, a working end 42 includes a reamer 50*d*, as shown in FIGS. 9 and 10, and is selected for engagement with tissue adjacent intervertebral space S. Male mating portion 48 of working end 42 having reamer 50*d* is releasably connected with female mating portion 44 of member 22 in a quick release configuration. Sleeve 60 is translated, in a direction shown by arrow A in FIG. 11, into the extended position to enclose reamer 50*d* to resist and/or prevent engagement of reamer 50*d* with tissue. Reamer 50*d* is disposed adjacent intervertebral space S. Sleeve 60 is translated, in a direction shown by arrow B in FIG. 12, into the retracted position to expose reamer 50*d*. Surgical instrument 12 is manipulated such that reamer 50*d* engages and/or disrupts the endplate tissue. In some embodiments, the disrupted tissue is removed. Sleeve 60 is translated, in a direction shown by arrow A in FIG. 11, into the extended position to enclose reamer 50*d* to resist and/or prevent engagement of reamer 50*d* with tissue. In some embodiments, surgical instrument 12 is manipulated to remove reamer 50*d* from adjacent intervertebral space S and/or the surgical site. Sleeve 60 is translated, in a direction shown by arrow B in FIG. 12, into the retracted position to expose reamer 50d. The quick release interchangeability of mating part 40 and end 42 facilitate disengagement reamer 50d from member 22, as described herein, such that an alternate working end may be intra-operatively interchanged and engaged with member 22 to perform an alternate step for treating vertebrae V.

Upon completion of the surgical procedure, the non-implanted components and assemblies of surgical system 10 are removed from the surgical site and the incision closed. In some embodiments, surgical instrument 12 is disassembled, as described herein, to facilitate cleaning of one or all of the components. Surgical instrument 12 may be re-assembled for use in a surgical procedure.

In some embodiments, surgical system 10 may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit.

In some embodiments, surgical system 10 may include one or a plurality of plates, connectors, spinal rods and/or bone fasteners for use with a single vertebral level or a plurality of vertebral levels. In some embodiments, surgical system 10 may include fastening elements configured for fixation with vertebrae to secure joint surfaces and components, and provide complementary stabilization and immobilization to a vertebral region.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the fixation elements with vertebrae V. The components of surgical system 10 can be made of radiolucent materials such as polymers. Radiomarkers may be included for identification under x-ray, fluoroscopy, CT or other imaging techniques, as described herein. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a tissue engaging element comprising a wire brush;
a motorized actuator;
a member connected with the actuator and including a mating part releasably engageable with the tissue engaging element, the member being configured to be interchangeable with a plurality of alternate tissue engaging elements; and
a sleeve connected with the member and configured for disposal of the tissue engaging element, the sleeve being movable between an extended position for disposal about the tissue engaging element and a retracted position to expose the tissue engaging element.

2. A surgical instrument as recited in claim 1, wherein the sleeve is axially translatable relative to the member in a first direction and a second opposing direction.

3. A surgical instrument as recited in claim 1, wherein the mating part includes a female mating part engageable with a male mating part of the tissue engaging element.

4. A surgical instrument as recited in claim 1, wherein the tissue engaging element includes a first surgical tool and a second surgical tool.

5. A surgical instrument as recited in claim 1, wherein the member includes an image guide that is configured to generate a signal representative of a position of the tissue engaging element.

6. A surgical instrument as recited in claim 1, wherein the member is configured for mating with alternate actuators.

7. A surgical instrument as recited in claim 1, wherein the plurality of alternate tissue engaging elements includes one or more of a wire brush, a drum rasp, a rotating cutter and a reamer.

8. A surgical instrument comprising:
a tissue engaging element comprising a drum rasp;
a motorized actuator;
a member connected with the actuator, the member including a mating part releasably engageable with the tissue engaging element, the member being configured to be interchangeable with a plurality of alternate tissue engaging elements; and
a sleeve connected with the member and configured for disposal of the tissue engaging element, the sleeve being movable between an extended position for disposal about the tissue engaging element and a retracted position to expose the tissue engaging element.

9. A surgical instrument as recited in claim 8, wherein the mating part includes a quick release connection with the tissue engaging element.

10. A surgical instrument as recited in claim 8, wherein the drum rasp comprises a rigid cylinder having cutting blades.

11. A surgical instrument comprising;
a tissue engaging element comprising a reamer including a hollow drill;
a motorized actuator;
a member connected with the actuator and including a mating part releasably engageable with the tissue engaging element, the member being configured to be interchangeable with a plurality of alternate tissue engaging elements; and
a sleeve connected with the member and configured for disposal of the tissue engaging element, the sleeve being movable between an extended position for disposal about the tissue engaging element and a retracted position to expose the tissue engaging element.

12. A surgical instrument as recited in claim 1, wherein the tissue engaging element is encased within the sleeve when the sleeve is in the extended position.

13. A surgical instrument as recited in claim 1, wherein a distal end of the sleeve extends distal to a working end of the tissue engaging element when the sleeve is in the extended position, the working end extending distal to the distal end when the sleeve is in the retracted position.

* * * * *